United States Patent [19]

Wingrove

[11] 4,206,767
[45] Jun. 10, 1980

[54] UROLOGICAL DRAINAGE MONITOR

[75] Inventor: Robert C. Wingrove, Afton, Minn.

[73] Assignee: Medical Devices, Inc., St. Paul, Minn.

[21] Appl. No.: 847,249

[22] Filed: Oct. 31, 1977

Related U.S. Application Data

[63] Continuation-in-part of Ser. No. 738,752, Nov. 4, 1976, abandoned.

[51] Int. Cl.² .............................................. A61B 5/00
[52] U.S. Cl. .................................. 128/762; 128/275; 73/219
[58] Field of Search ........................ 128/214 C–214 E, 128/2 F, 2 G, DIG. 13, 275–276, 295, 272, DIG. 5, 760, 762, 670, 672; 73/195–197, 219; 239/66–70; 141/237, 244

[56] References Cited

U.S. PATENT DOCUMENTS

| | | | |
|---|---|---|---|
| Re. 26,964 | 10/1970 | Coanda | 128/2 |
| 2,648,981 | 8/1953 | Drake, Jr. | 73/215 |
| 3,043,303 | 7/1962 | Still | 128/214 |
| 3,194,069 | 7/1965 | Scott | 73/219 |
| 3,362,222 | 1/1968 | Johnson et al. | 73/198 |
| 3,450,153 | 6/1969 | Hildebrandt et al. | 137/486 |
| 3,561,427 | 2/1971 | Profy | 128/2 |
| 3,566,930 | 3/1971 | Kirschner | 141/244 |
| 3,578,245 | 5/1971 | Brock | 239/66 |
| 3,633,422 | 1/1972 | Grieshaber | 73/219 |
| 3,722,502 | 3/1973 | Besuner et al. | 128/2 F |
| 3,754,220 | 8/1973 | Sztombi et al. | 128/DIG. 13 |
| 3,769,497 | 10/1973 | Frank | 235/92 FL |
| 3,774,762 | 11/1973 | Lichtenstein | 210/321 B |
| 3,818,895 | 6/1974 | Stewart | 128/2 F |
| 3,831,453 | 8/1974 | McWhorter | 73/427 |
| 3,848,581 | 10/1974 | Cinqualbre et al. | 128/2 F |
| 3,874,850 | 4/1975 | Sorensen et al. | 23/230 B |
| 3,894,845 | 7/1975 | McDonald | 23/253 R |
| 3,912,455 | 10/1975 | Lichtenstein | 128/2 F X |
| 3,961,529 | 6/1976 | Hanifl | 73/219 |
| 3,989,066 | 10/1976 | Sturman et al. | 137/624.2 |
| 4,018,224 | 4/1977 | Kurtz et al. | 128/276 |

FOREIGN PATENT DOCUMENTS

2255878   7/1975  France .................................. 128/2 F

Primary Examiner—Robert W. Michell
Assistant Examiner—Francis J. Jaworski
Attorney, Agent, or Firm—Merchant, Gould, Smith, Edell, Welter & Schmidt

[57] ABSTRACT

A drainage monitor including a collector and a control unit. The collector has a lower, storage section made up of elongated parallel vertical chambers, a liquid manifold section above the chambers with a plurality of taps aligned with the chambers, and collapsible conduits connecting the taps with the chambers. The control unit includes an arrangement for supporting the collector, chamber valving apparatus aligned with the conduits and operable to compress them so as to prevent liquid flow, releasable solenoid-and-latch apparatus for preventing operation of the valving apparatus, and electrical timing circuitry for releasing the releasable apparatus in a predetermined sequence.

19 Claims, 11 Drawing Figures

UROLOGICAL DRAINAGE MONITOR

This is a continuation-in-part of my co-pending application which was filed in the U.S. Patent and Trademark Office of date Nov. 4, 1976, under Ser. No. 738,752, now abandoned.

BACKGROUND OF THE INVENTION

This invention relates to the field of medicine, and particularly to apparatus whereby medical personnel may collect and keep convenient and reliable record of, the liquid output of a patient, and extract samples of the liquid without compromising the sterility of the apparatus. The equipment is especially designed for monitoring the volumetric urine output of a patient at regular hourly intervals for a total period longer than the usual work shift of hospital personnel.

The importance of knowledge of the patient's renal output is well-known in medicine. A knowledge of the volumes of urine excreted by a patient over particular periods of time is extremely helpful in the management of fluid imbalances or electrolyte abnormalities. In cases where the patient has been in shock and the renal function is questionable, as in severe burn cases, urine output measurement is very important. Also, in virtually any serious illness or injury or operational procedure where a reduction in blood volume is anticipated, accurate measurement of small urinary volume output is either mandatory or highly desirable.

Accurate urine measurements are an aid in recognizing the onset of impending post-surgical shock. For this reason, the urine volumes of many post-surgical patients are measured hourly, particularly those who have undergone cardiac, thoracic, neurological, or genitourinary surgery.

SUMMARY OF THE INVENTION

Numerous structures are known for monitoring the renal output of the patient, from a simple graduated cylinder at the end of the indwelling catheter to a highly mechanized arrangement such as that of Scott U.S. Pat. No. 3,194,069, for example. My monitoring arrangement has the advantages of completely automatic operation to collect in sequential chambers the excretions for ten successive hours, in a form resembling a bar graph for convenient observation, with provisions for sampling the liquid in any chamber at any time, in a closed or sealed system adapted either for emptying and resterilizing or for disposable use, the manipulations at the end of the total collecting period to prepare for a second collection period being simple, convenient and sanitary. Provision is made for applying suction if this is desired, and the arrangement includes a control unit powered by a battery which is rechargeable for long service.

Various advantages and features of novelty which characterize my invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there are illustrated and described two preferred embodiments of the invention.

DESCRIPTION OF THE FIRST EMBODIMENT

Figures 1, 2, 3:
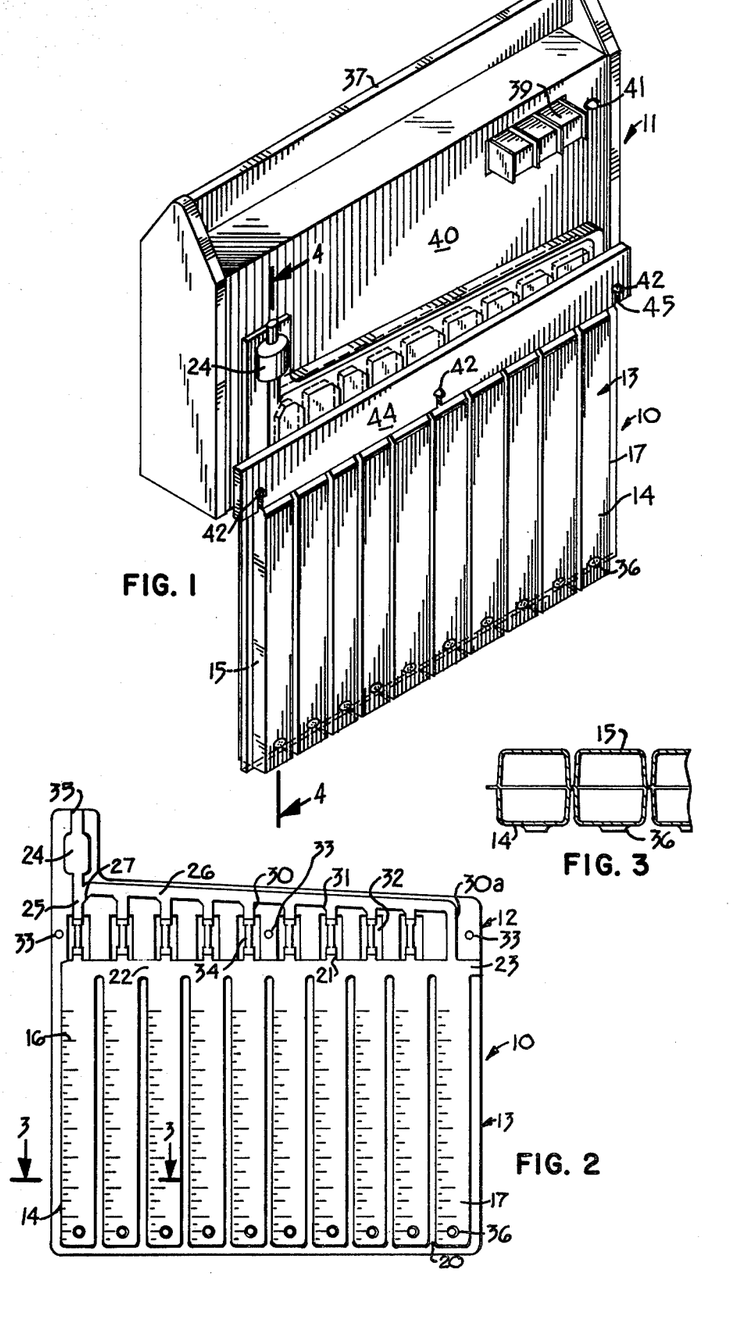
FIG. 1, is a view of a first embodiment of my invention in perspective.
FIG. 2 is a showing in elevation of a portion of the invention.
FIG. 3 is a fragmentary sectional view taken along the line 3—3 of FIG. 2, to a larger scale.

As shown in FIGS. 1-7, my monitor comprises a collector 10 and a control unit 11 which supports the collector and controls the flow of liquid thereto. As shown in FIG. 2, collector 10 has an upper, manifold section 12 and a lower, storage section 13. The collector is formed of relatively rigid plastic such as a vinyl resin, and may be constructed from two sheets 14 and 15 of material sealed together around their edges and at other locations as necessary. Each of front sheet 14 and back sheet 15 is preformed so that together they define the chambers and passages about to be described. Preferably, front sheet 14 is transparent and colorless, and carries volume graduations 16, while back sheet 15 is translucent and white.

Storage section 13 comprises a plurality of vertically elongated chambers 17 separated by spacing walls 20 and having individual upwardly directed nipples 21 at their upper ends. A common space 22 connects all the chambers near their upper ends, and a lateral opening 23 is formed in one end wall of the collector.

Manifold section 12 comprises an inlet connection in the form of a drip chamber 24 extending downward to a tap 25. A generally horizontal passage or header 26 slopes slightly downward away from tap 25, to which it is connected at a sharp downward angle at 27. A plurality of further taps 30 extend downward from passage 26 in line with the nipples of chambers 17, in a sequence counting to the right from tap 25, the final tap 30a being in fact integral with the nipple of the final chamber. Taps 30 are not simple right angle connections, but are formed as at 31, so that liquid flowing to the right in the passage tends to flow into the taps rather than pass by them, as will be explained more fully below.

Cutouts 32 are formed in the front and back sheets between nipples 21 and taps 25, 30, and supporting apertures 33 are provided in the sheets at each end and centrally of the row of cutouts. A plurality of collapsible tubes 34 are connected at their upper ends to taps 25, 30, and at their lower ends to nipples 21, so that liquid may flow from passage 26 into any of the storage chambers 17. Drip chamber 24 is formed at its upper end 35 to receive the end of an in-dwelling catheter or other liquid source, not shown, and outlet 23 is similarly formed to receive an overflow or suction tube, also not shown, or a pledget of cotton to prevent contamination of the collector, which accordingly acts in the closed or sealed mode.

Some or all of the chambers may be provided near their bottoms with external self-sealing patches 36, to permit insertion of a sampling needle without subsequent leakage.

Control unit 11 comprises a metallic housing which encloses the battery and electrical circuitry of the system, and includes at its top a handle 37 by which the monitor can be conveniently carried or supported, from a bed rail, for example. Its front panel 40 carries a signal lamp 41, a battery control switch 39, and such other controls as may be desired for circuit refinements not pertinent to the overall invention here. The housing may also be provided with a connection for supplying charging energy for the system battery, as is known in battery a ctuated equipment.

A plurality of support pins 42 project from the lower part of the front panel, spaced for engagement with apertures 33 in collector 10, so that chambers 17 are below the unit, and a recess 43 may be provided in panel 40 to accommodate chamber 24, as suggested in FIG. 4.

A bar 44 of rigid material is located outside collector 10 in the area of cutouts 32 and tubes 34, and is carried on pins 42, with which it cooperates to comprise support means for collector 10: bar 44 may be separate and metallic, or may be molded as a portion of front sheet 14. In the embodiment shown in FIGS. 1, 4 and 5 a removable metal bar is provided with slots 45 which fit into grooves 46 in pins 42, where it is held gravitationally by its own weight: alternative fastening methods may be used as desired.

A row of chamber valving means 49 extends across the bottom of unit 11 for alignment with tubes 34 of collector 10. For each tube 34, there is an actuator 50 urged towards the tube by a spring 51 and having a finger 52 which extends through an opening 53 in panel 40 to engage the tube. The force of springs 51 is sufficient to cause fingers 52 to compress tubes 34 against bar 44 so as to prevent the flow of liquid through the tubes, as shown in FIG. 5. A cushion 54 is also provided.

Figures 4, 5:
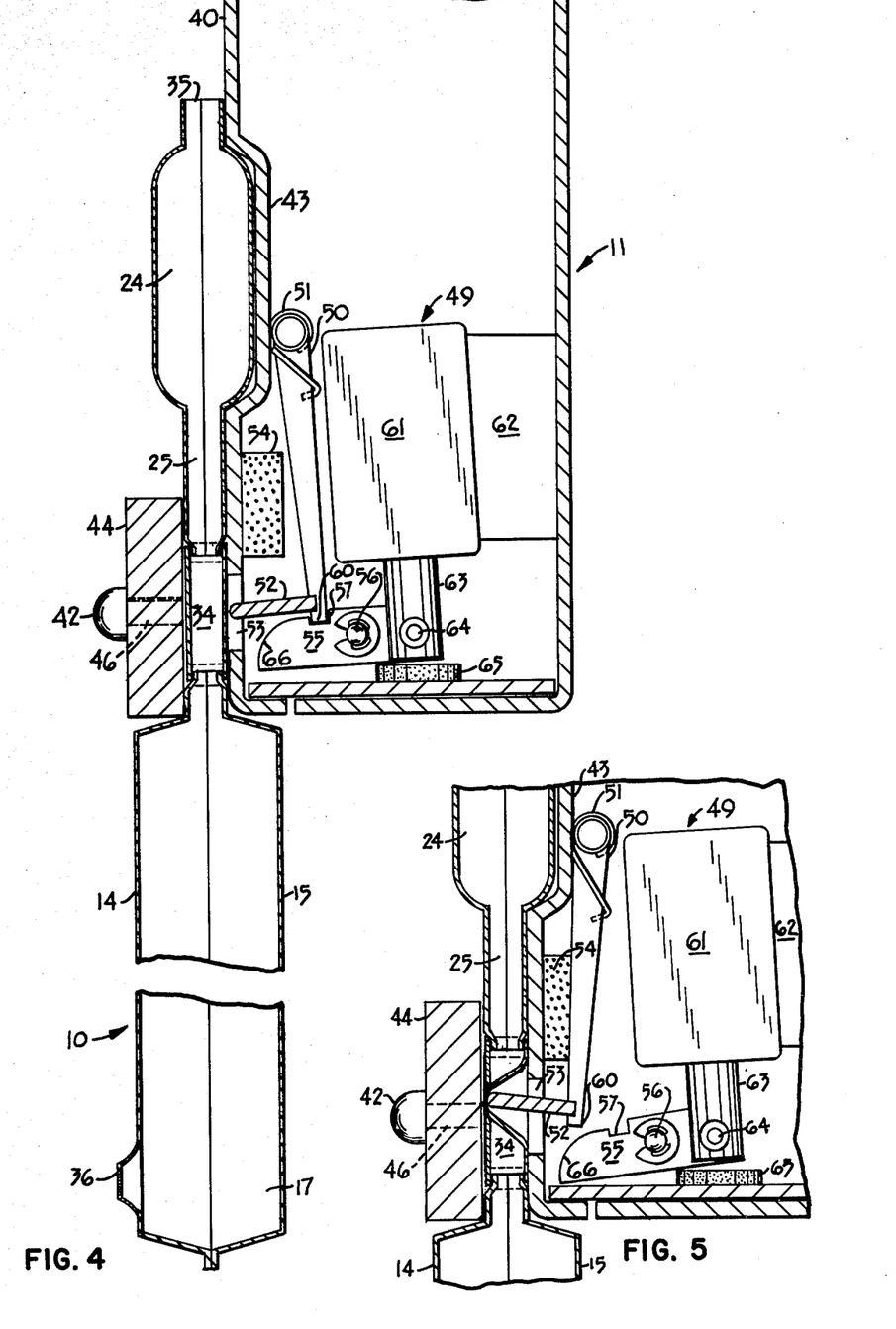
FIG. 4 is a sectional view along the line 4—4 of FIG. 1 to a larger scale.
FIG. 5 is a fragmentary view like FIG. 4, showing a different position of parts of the invention.

Each actuator 50 is normally retained in the position shown in FIG. 4 by means including a latch 55 pivoted at 56 and having a notch 57 to receive the tip 60 of the actuator. Movement of latch 55 is accomplished by a solenoid 61 mounted on a bracket 62 and having an actuator 63 pivoted to latch 55 at 64. A cushion 65 is provided here also. Actuator 63 is normally retained, by resilient means not shown, in the position shown in FIG. 4. Notch 57 is square-walled, but the front top portion of latch 55 is curved downwardly at 66. Momentary energization of relay 61 pivots latch 55 to release actuator 50, the parts then taking the position shown in FIG. 5.

Figure 6:
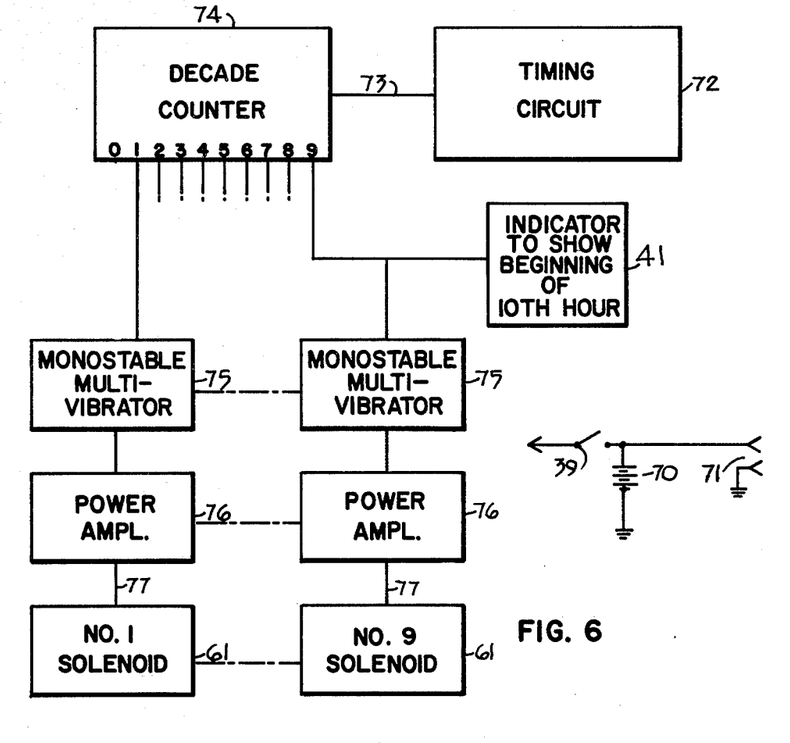
FIG. 6 is a schematic diagram showing the electrical portion of the invention.

FIG. 6 is a schematic showing of the circuitry contained in unit 11. Electrical energy for the various circuit elements is obtained from a battery 70 arranged for recharging through a connection 71, and controlled by switch 39. A timing circuit 72 of any suitable design supplies one pulse per hour on a cable 73 to a decade counter 74 of the type which resets itself to zero when de-energized. The zero count output of the counter 74 is not used: to each of the other outputs there are connected a monostable multivibrator 75 and a power amplifier 76, the latter being connected through a cable 77 to one of the solenoids 61. The solenoids are connected in sequence beginning with the one nearest drip chamber 24. Also connected to the nine count output of counter 75 is signal lamp 41, which lights to indicate the beginning of the tenth hour.

It will be apparent that timing circuit 72 may perform further functions not involved in the present invention.

Operation of the First Embodiment

To use my invention, a control unit having an adequately charged battery is carried to the site of use and secured by handle 37 to a suitable support, such as a bed rail. Bar 44 is removed, exposing openings 53, and actuators 50 are manually pressed inward until their tips depress latches 55 and are engaged by notches 57. A collector 10 is now supported on pins 42 by its apertures 33, and bar 44 is replaced in the grooves in pins 42. If desired, an overflow tube is inserted in opening 23 and an overflow vessel is provided therebelow, or a suction tube may be connected to opening 23 if the condition of use of the monitor warrants. The discharge end of an in-dwelling catheter or other liquid source is connected to the upper end 35 of drip chamber 24, and switch 39 is turned on, beginning operation of timing circuit 72. Liquid discharge drops through chamber 24, tap 25, tube 34, and nipple 21, into the first, lefthand chamber 17 of collector 10. Its quantity, color, and so forth can be visually observed, and if sampling is desired, a needle may be thrust into the chamber through patch 36 to extract liquid from the chamber.

At the end of an hour, timing circuit 72 supplies a pulse to counter 74, which in turn supplies a signal on the first count lead to multivibrator 75, which acts through power amplifier 76 to energize solenoid 61 associated with the chamber valving of the lefthand chamber. Latch 55 is pivoted in a counter-clockwise direction, releasing actuator 50 to close off tube 34 by compression against bar 44. At the end of the multivibrator pulse, solenoid 61 is de-energized, but actuator 50 remains in its operated position. Liquid continues to drip into tap 25 until it fills with liquid, which then rises at 27 into passage 26 and flows into the first tap 30, which conducts the liquid through tube 34 and nipple 21 to drip into the second chamber 17. At the end of the second hour, timing unit 72 supplies second signal to counter 74, which now supplies an output on the second count conductor to cause the solenoid of the second chamber valving means to release its actuator, and this process continues.

Figure 7:
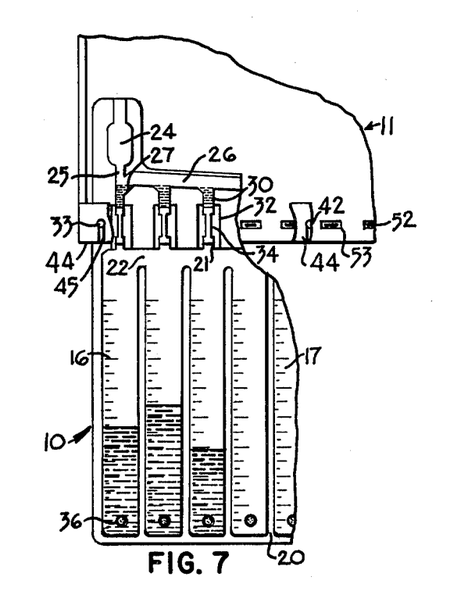
FIG. 7 is a fragmentary view of the invention in use.

FIG. 7 is a fragmentary view showing the appearance of the apparatus shortly after the end of the third hour. Liquid has been collected in the first three chambers, and the first three taps also contain liquid: newly excreted liquid now flows along passage 26 to drip into the fourth chamber. It will, of course, be understood, that the graduations on each chamber take into account the liquid trapped in the preceeding tap 27, 30.

It will be evident that the monitoring system presents very clearly to medical personnel, in bar graph or histogram form, and natural color, the rendal function of the patient, that sampling is available at any time without disturbing the patient or the monitoring equipment, and that liquid from the drip chamber cannot pass into a given collecting chamber until the taps leading to all preceeding chambers are closed and filled with liquid.

As shown in the drawing, collector 10 is provided with ten chambers 17, to allow for changing collectors once during each eight-hour shift for the nursing personnel. To perform the change, it is only necessary to turn off the switch 39, lift bar 44, disconnect the catheter tube at 35, and remove the collector with its contents. After manually resetting the actuators 50, a new collector is suspended on pins 42, bar 44 is replaced, the catheter is reconnected at 35, and switch 39 is then turned on. This is a clean, convenient procedure, causing minimum annoyance to patients and medical personnel. If such a regular changing procedure is followed, there is no need for an overflow tube or container.

Sometimes, however, emergencies arise which prevent the changing of the collector at eight-hour intervals. At the end of the eighth hour, flow of liquid is directed into the ninth chamber. At the end of the ninth hour, flow of liquid is directed into the tenth chamber, and lamp 41 is illuminated to attract the attention of medical personnel. At the end of the tenth hour, no further operation is possible from the valving apparatus, and the fluid continues to pass into the last chamber until it overflows at opening 23. This opening also functions to afford egress for liquid poured from the collector at the end of its period of use. While it may be possible to clean and sterilize these collectors, it is more desirable simply to dispose of them in a suitable fashion.

Description of the Second Embodiment

FIGS. 8–11 show a second embodiment of the invention, in which my monitor 80 comprises a collector 81 and a control unit 82 which supports the collector and controls the flow of liquid thereto. Collector 81 is made up of a storage section 83 and a manifold section 84, interconnected by a bridging member 85, all being made of relatively rigid plastic such as a vinyl resin.

Figure 8:
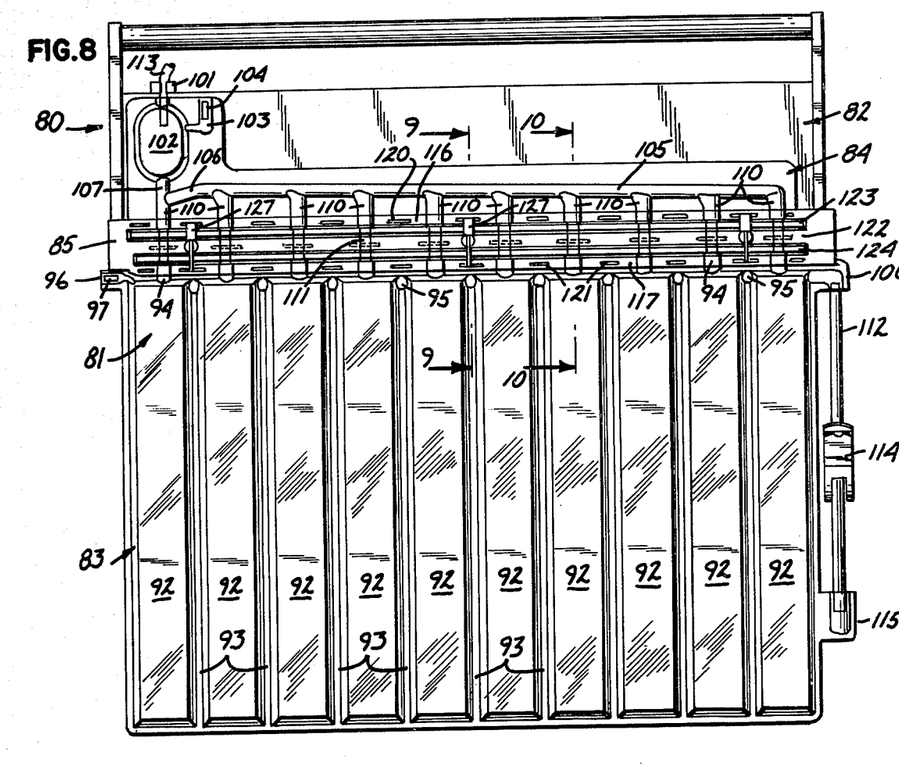
FIG. 8 is a view in elevation of a second embodiment of the invention.

Storage section 83 is constructed from two sheets 86 and 87 of material sealed together around their edges and at other locations as necessary, and preformed so that together they define the chambers and passages about to be described. Manifold section 84 is constructed from sheets 90 and 91 of material preformed and sealed in the same general fashion.

Storage section 83 comprises a plurality of vertically elongated chambers 92 separated by spacing walls 93 and having individual upwardly directed nipples 94 at their upper ends. They are also provided with tubular interconnections 95 at their upper ends. A breather opening 96 is provided at one edge of the storage section, and receives an air filter 97. An outlet nipple 100 is formed at the other edge of section 83.

Manifold section 84 comprises an inlet nipple 101 opening into a drip chamber 102: a breather opening 103 is provided here also and receives an air filter 104. A header 105 in section 84 slopes downward in both direction from a location 106 adjacent chamber 102, and is connected at 107 to the drip chamber. A plurality of taps 110 are spaced along header 105 in alignment with nipples 94 of chambers 92, in a sequence counting to the right from drip chamber 102 in FIG. 8.

The front and back sheets of the two sections are sealed together under pressure in a suitable radio frequency sealing apparatus. Before sealing section 83, first ends of a plurality of valvable means in the form of collapsible elastic tubes 111 are inserted into nipples 94, and a like overflow tube 112 is inserted into nipple 100, so that after sealing the tubes are tightly secured to the storage unit.

Likewise, before sealing section 84, the other ends of tubes 111 are inserted into taps 110, and an inlet tube 113 is inserted into inlet nipple 101, so that after sealing the tubes are tightly secured to the manifold section, and interconnect the sections for passage of liquid between them. Tube 112 is provided with a pinch clamp 114, and its free end is removably secured in a pocket 115 formed in storage section 83.

Figures 9, 10, 11:
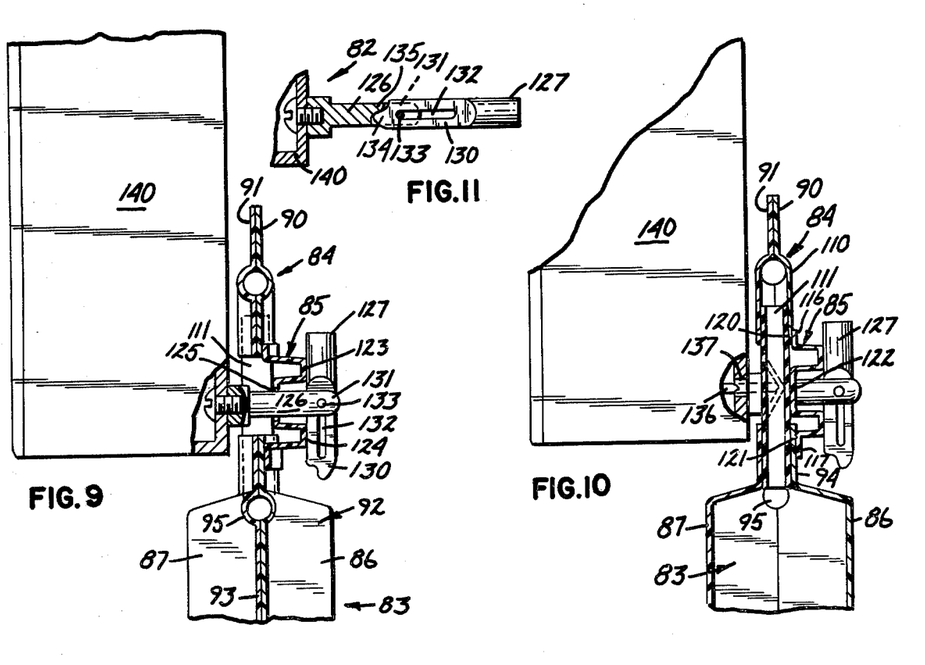
FIGS. 9 and 10 are fragmentary section views along lines 9—9 and 10—10 of FIG. 8.
FIG. 11 shows a detail.

Bridging member 85 has a pair of longitudinal flanges 116 and 117 which are sealed to sections 83 and 84 at areas 120 and 121 respectively, and a mid-section 122 between spaced reinforcing ribs 123 and 124. Mid-section 122 is provided with apertures 125 centrally and near its ends, by which collector 81 may be suspended from a set of studs 126, mounted on and projecting from control unit 82, and having latching tips 127 with flat tongues 130 sliding between shoulders 131 of studs 126, and slotted at 132 to pass cross pins 133 of the studs. When the tips are turned as shown in FIG. 11, abutments 134 of the tongues engage abutments 135 of the studs, and a collector may be installed on the studs by sliding apertures 125 thereover. Then if tips 127 are pivoted about pins 133 and allowed to slide downward, the tips engage ribs 123 and 124 of member 85 so that the collector is securely but removably suspended from the control unit.

As best shown in FIG. 10, control unit 82 is provided as before with valving means including actuator fingers 136 which may extend through apertures 137 in the housing 140 of the unit. Midsection 122 of bridging member 85 is positioned to engage the surfaces of tubes 111 opposite fingers 136, and is stiff enough to function, as did bar 44 of the first embodiment, to resist the force of fingers 136 and enable them to valve tubes 111 into the collapsed condition shown in broken lines in FIG. 10, in which no liquid may pass from the header to the chambers below.

The configuration of header 105 is functionally the same as that previously described.

Operation of the Second Embodiment

The second embodiment of the invention operates essentially in the same manner as that previously described, the principal difference being the detailed construction of the collector and its method of support on the control unit, which is otherwise the same. Actuator tips 139 are pressed inward until they latch. A collector 81, with filters 97 and 104 and pinch clamp 114 in place, and with the end of tube 114 in pocket 115, is secured to the control unit by pivoting stud latch tips 127 into the FIG. 11 position, sliding apertures 125 of bridging member 85 across studs 126, and returning tips 127 to the FIG. 9 position.

Now if the discharge end of an in-dwelling catheter is connected to 113, the collection and display of liquids is the same in this embodiment of the invention as was described in detail in connection with the preceeding embodiment.

From the foregoing, it will be evident that I have invented a new and wholly automatic arrangement for convenient and sterile monitoring of liquid discharges, particularly discharges of urine, from patients in hospitals. My arrangement enables ready inspection and sampling of the liquid collected, and is quickly and conveniently affixed to any hospital bed and easily used, with a minimum of training, by hospital personnel.

Numerous characteristics and advantages of my invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

What is claimed is:

1. In a drainage monitor for receiving and displaying the urinary output of a subject;
   a unitary array of elongated parallel closed storage chambers in fixed, side by side relationship, said chambers having individual input nipples in first ends thereof;
   a continuous header of greater than capillary diameter passing transversely with respect to said first ends of said chambers and having a plurality of taps spaced therealong;
   collapsible conduit means connected to conduct liquid from said taps to said nipples;
   means affording an inlet connection to said header at one end thereof;
   support means for suspending said chambers and said header with said chambers extending vertically below said header;
   and valving means external to said conduit means for enabling and preventing passage of liquid therethrough.

2. A structure according to claim 1 in which said header is configured to prevent flow of liquid in said header beyond the first chamber in sequence enabled to receive said liquid.

3. A structure according to claim 1 in which said valving means includes a timer.

4. A structure according to claim 1 including manifold section which comprises said header and said inlet connection, said header extending from said inlet connection in a direction such that said taps become increasingly short and said taps being connected thereto in such a fashion that liquid does not flow into a tap from said inlet until all previous taps are full of liquid.

5. A structure according to claim 1 in which said chambers and said header are integral.

6. A structure according to claim 1, in which the valving means includes
   (a) actuator means normally operative to prevent passage of liquid through said conduit means,
   (b) releasable means for preventing operation of said actuator means, and
   (c) control means for releasing said releasable means to enable operation of said actuator means.

7. In a urinary drainage monitor:
   (1) a substantially flat liquid collector comprising
      (a) a storage section including a unitary array of elongated, parallel chambers in fixed side-by-side relationship, said chambers having individual input nipples in first ends thereof,
      (b) a continuous header of greater than capillary diameter passing transversely of said first ends of said chambers and having a plurality of taps spaced therealong in a predetermined sequence, and
      (c) collapsible conduit means connected to conduct liquid from said taps to said nipples; and
   (2) a control unit comprising
      (a) support means for suspending said collector for visual observation with said chambers extending vertically below said header,
      (b) chamber valving means positioned for alignment with said conduit means and including individual contact fingers resiliently operable into collapsing engagement therewith to thereby prevent passage of liquid therethrough,
      (c) releasable means for preventing operation of said valving means, and
      (d) control means for releasing said releasable means in said predetermined sequence to enable operation of said valving means.

8. A structure according to claim 7 in which said valving means are arranged to collapse said conduit means against a portion of said support means.

9. A structure according to claim 7 in which said control unit comprises a housing containing said valving means and said releasable means, and is provided with apertures through which the valving means engage said collapsible conduit means.

10. A structure according to claim 7, including rigid means engaging the sides of said conduit means remote from said control unit in alignment with said valving means.

11. In a drainage monitor;
    (1) a substantially flat liquid collector comprising
       (a) a storage section including a unitary array of elongated, parallel chambers in fixed side-by-side relationship, said chambers having individual input nipples in first ends thereof;
       (b) a continuous header of greater than capillary diameter passing transversely of said first ends of said chambers and having a plurality of taps spaced therealong in a predetermined sequence, and
       (c) collapsible conduit means connected to conduct liquid from said taps to said nipples; and
    (2) a control unit comprising
       (a) support means for suspending said collector with said chambers extending vertically below said header,
       (b) chamber valving means positioned for alignment with said conduit means and including individual contact fingers resiliently operable into collapsing engagement therewith to thereby prevent passage of liquid therethrough;
       (c) releasable means for preventing operation of said valving means, and
       (d) control means for releasing said releasable means in said predetermined sequence to enable operation of said valving means,
       (e) said support means including rigid means engaging the sides of said conduit means remote from said control unit in alignment with said valving means, in which said rigid means is integral with said chambers and said header.

12. A liquid collector comprising:
    a storage section having a unitary array of elongated storage chambers in substantially flat side-by-side relation for separately receiving and displaying liquid, said chambers having individual inlet nipples in first ends thereof;
    a manifold section integral with said storage section and having an inlet for liquid, an elongated header connected to said inlet, and a plurality of liquid discharge openings positioned along said header;
    discrete collapsible conduit means interposed between said discharge openings and said nipples for connecting said chambers severally to said openings to enable and prevent flow of liquid therebetween; and
    support means for suspending said collector with said chambers extending vertically below said header, and with said header sloping downwardly from said inlet.

13. A structure according to claim 12, including passage means and interconnecting said first ends of said chambers, said passage means being continued beyond the end of a chamber remote from said inlet, as an outlet from said storage section.

14. A structure according to claim 12 in which said storage chambers define front and rear surfaces and the front surface of said storage section being at least partly transparent, and the rear surface of said storage section being translucent and white so that different levels of visible fluids in said chambers give the visual appearance resembling a histogram.

15. A structure according to claim 14 in which said front of said storage section bears graduations correlated with the volumes of said chambers, measured from second ends thereof when the chambers are vertical, augmented by the volume of said header between said chamber.

16. A structure according to claim 12, in combination with a control unit comprising
- support means for suspending said liquid collector with said chambers extending vertically, and
- valving means positioned to engage said collapsible conduit means externally for enabling and preventing passage of liquid therethrough.

17. A structure according to claim 16 in which the valving means includes
  (a) actuator means normally operative to prevent passage of liquid through said conduit means,
  (b) releasable means for preventing operation of said actuator means, and
  (c) control means for releasing said releasable means to enable operation of said actuator means.

18. A liquid collector comprising a manifold section and a storage section physically unitary therewith, said sections being formed from front and rear substantially rigid plastic members sealed together along their edges and elsewhere to define in said storage section a plurality of elongated chambers and in said manifold section an inlet, a header, and a plurality of taps,
- said chambers being in parallel, substantially flat, side-by side relationship and extending away from said manifold section, the ends of said chambers nearest said manifold section being provided with nipples extending lengthwise from said chambers, in which said sections are cut away between said nipples and said openings,
- and valvable means comprising collapsible tubes spanning the cut away portions.

19. Collection apparatus for displaying, in histographic form, the renal output of a patient as a function of time, comprising, in combination, a storage section, a manifold section, and collapsible means interconnecting said sections, each of said sections being formed from front and rear substantially rigid plastic members sealed together along their edges and elsewhere to define in said storage section a plurality of elongated chambers and in said manifold section an inlet, a header, and a plurality of taps,
- said chambers being in parallel, substantially flat, laterally apposed spaced relationship extending away from said manifold section, the ends of said chambers nearest said manifold section being provided with nipples extending lengthwise from said chambers,
- and said inlet, said header, and said taps being interconnected in fluid conducting relationship, with said taps positioned in alignment with and spaced from said nipples.

* * * * *

UNITED STATES PATENT AND TRADEMARK OFFICE
CERTIFICATE OF CORRECTION

PATENT NO. : 4,206,767
DATED : June 10, 1980
INVENTOR(S) : Robert C. Wingrove

It is certified that error appears in the above-identified patent and that said Letters Patent are hereby corrected as shown below:

Column 4, line 57, "rendal" should be --renal--;

Column 5, line 50, "tion" should be --tions--;

Column 3, line 15, "a ctuated" should be --actuated--;

Claim 4, line 1, after "including" insert --a--.

Signed and Sealed this

Thirtieth Day of September 1980

[SEAL]

Attest:

SIDNEY A. DIAMOND

Attesting Officer

Commissioner of Patents and Trademarks